United States Patent [19]
Bloch et al.

[11] 4,018,836
[45] Apr. 19, 1977

[54] PRODUCTION OF MONOCHLORO-SUBSTITUTED SATURATED COMPOUNDS

[75] Inventors: Herman S. Bloch, Skokie; Louis Schmerling, Riverside, both of Ill.

[73] Assignee: UOP Inc., Des Plaines, Ill.

[22] Filed: June 21, 1976

[21] Appl. No.: 698,238

Related U.S. Application Data

[63] Continuation-in-part of Ser. No. 507,086, Sept. 18, 1974, abandoned.

[52] U.S. Cl. .......................................... 260/648 R
[51] Int. Cl.² ............... C07C 17/26; C07C 23/10; C07C 23/24
[58] Field of Search ....... 260/651 R, 658 R, 648 R, 260/658 C

[56] References Cited

UNITED STATES PATENTS 2,562,369   7/1951   Schmerling et al. ............ 260/648 R Primary Examiner—D. Horwitz
Attorney, Agent, or Firm—James R. Hoatson, Jr.; Raymond H. Nelson; William H. Page, II

[57] ABSTRACT

Monochloro-substituted saturated compounds may be prepared by condensing a saturated compound such as cycloalkyl hydrocarbon with a chloromonoolefin possessing not more than 4 carbon atoms and having the chlorine atom attached to one of the doubly-bonded carbon atoms in the presence of a free radical-generating catalyst and a promoter comprising a hydrogen chloride compound.

8 Claims, No Drawings

PRODUCTION OF MONOCHLORO-SUBSTITUTED SATURATED COMPOUNDS

CROSS-REFERENCE TO RELATED APPLICATIONS

This application is a continuation-in-part of our co-pending application Ser. No. 507,086 filed Sept. 18, 1974, and now abandoned, all teachings of which are specifically incorporated herein by reference thereto.

BACKGROUND OF THE INVENTION

The free radical-induced reaction of a saturated hydrocarbon with an unsaturated hydrocarbon is well known in the prior art. In addition, the prior art as exemplified by U.S. Pat. No. 2,562,369 has disclosed that a saturated hydrocarbon may be condensed with an olefin containing at least one chlorine atom on each of the doubly-bonded carbon atoms in the presence of a free radical generator to form an unsaturated chlorinated hydrocarbon. However, this prior art patent stated that it is essential that the chloroolefin contain at least two chlorine atoms per molecule since monochloroolefins do not give a condensation reaction of the type therein described. This belief, that the condensation required an olefinic compound possessing at least one halogen radical on each of the doubly-bonded carbon atoms, would lead one reasonably skilled in the art away from the discovery that the condensation between a saturated hydrocarbon and a chloromonoolefin in which the chlorine atom is attached to only one of the doubly-bonded carbon atoms may be effected in the presence of a free radical-generating compound and a promoter.

This invention relates to a process for the production of monochloro-substituted saturated compounds. More specifically, the invention relates to a process for the preparation of monochloro-substituted saturated compounds which comprises condensing a cycloalkyl hydrocarbon with a chloromonoolefin in which the chlorine atom is attached to one of the doubly-bonded carbon atoms, said condensation being effected in the presence of a free radical-generating catalyst and a promoter comprising a hydrogen chloride compound.

As was hereinbefore set forth, it has now been unexpectedly discovered that a saturated compound such as a cycloalkyl hydrocarbon may be condensed with a chloromonoolefin in which a chlorine atom is attached to only one of the doubly-bonded carbon atoms, the condensation being induced by a free radical-generating catalyst such as a peroxy compound and in the added presence of a promoter comprising a hydrogen chloride compound. The utilization of the promoter comprising the hydrogen chloride compound will produce a greater percentage conversion of the original reactants, namely, the saturated compound and the chloroolefin compound, and increase the yield of the monochloro-substituted saturated compound.

The products which are obtained by the condensation reaction of the present invention, namely, monochloro-substituted saturated compounds, are utilized in the chemical industry in various ways. For example, the heavier weight molecular monochloro-substituted saturated compounds may be converted to alcohols for further use in the preparation of detergents. Likewise, 2-chloroethylcyclohexane which may be prepared according to the process of this invention may be used as an intermediate for the preparation of phenylated ethylcyclohexane.

It is therefore an object of this invention to provide a process for the preparation of monochloro-substituted saturated compounds.

A further object of this invention is to provide an improved process for the obtention of a monochloro-substituted saturated compound by the use of a promoter thereby permitting more economic batch and continuous type processes to be employed.

In one aspect an embodiment of this invention resides in a process for the production of a monochloro-substituted saturated compound which is effected by condensing a saturated cycloalkyl hydrocarbon selected from the group consisting of a cycloalkane having from 5 to about 8 carbon atoms in the ring, a bicycloalkyl having from 10 to 16 carbon atoms in the rings and a polycycloalkane having from 6 to 14 carbon atoms in the rings with a chloromonoolefin possessing not more than 4 carbon atoms and having the chlorine atom attached to one of the doubly-bonded carbon atoms, in the presence of a free radical-generating peroxide catalyst at a temperature at least as high as the decomposition temperature of said catalyst and at a pressure of from 1 to about 100 atmospheres, and recovering the resultant monochloro-substituted saturated compound, and with the improvement which comprises effecting the reaction in the presence of a promoter comprising hydrogen chloride.

A specific embodiment of this invention is found in a process for preparing (2-chloroethyl)cyclohexane which comprises condensing cyclohexane with vinyl chloride at a temperature in the range of from about 130° to about 140° C. in the presence of a catalyst comprising di-t-butyl peroxide and a promoter comprising a hydrogen chloride compound and recovering the resultant (2-chloroethyl)cyclohexane an x-(1-chloroethyl)-y-(2-chloroethyl)cyclohexane.

Other objects and embodiments will be found in the following further detailed description of the present invention.

As hereinbefore set forth the present invention is concerned with a process for preparing monochloro-substituted saturated compounds in which a saturated compound comprising a cycloalkyl hydrocarbon is condensed with a monochloromonoolefin in which the chlorine atom is attached to one of the doubly-bonded carbon atoms in the presence of a free radical-generating catalyst and in the presence of a promoter comprising a hydrogen chloride compound. For purposes of this invention, the term "cycloalkyl hydrocarbon" as used in the present specification and appended claims will refer to monocycloalkanes, polycycloalkanes, and bicycloalkyls. As examples of these compounds, a cycloalkyl hydrocarbon may be exemplified by cyclohexane,

a polycycloalkane may be exemplified by decahydronaphthalene

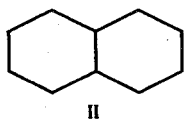

II and by bicyclo[2.2.1]heptane

III and a bicycloalkyl may be exemplified by bicyclohexyl

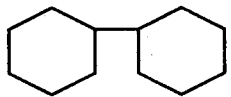

IV

Each of these may contain alkyl substituents having from 1 to about 10 or more carbon atoms.

The reaction is effected under conditions which include an elevated temperature of at least as high as the initial decomposition temperature of the free radical-generating catalyst. In addition, another reaction condition involves pressure, said pressure ranging from about atmospheric to about 100 atmospheres or more. When superatmospheric pressures are employed, said pressures are afforded by the introduction of vaporized reactants or a substantially inert gas such as nitrogen into the reaction zone. Another variable which is employed is the amount of reactants, the saturated compound comprising a cycloalkyl hydrocarbon usually being present in a mole ratio in the range of from about 1:1 to about 10:1 moles per mole of monochloromonoolefin in which the chlorine atom is attached to one of the doubly-bonded carbon atoms.

Examples of suitable saturated compounds comprising cycloalkyl hydrocarbons which are utilized as one of the starting materials in the process of this invention include monocycloalkanes containing from 5 to about 8 carbon atoms in the ring such as cyclopentane, cyclohexane, cycloheptane, cyclooctane; polycycloalkanes having from 6 to 14 carbon atoms in the ring such as bicyclo[2.2.1]heptane, decahydronaphthalene, tetradecahydroanthracene, bicycloalkyls having from 10 to 16 carbon atoms in the ring such as bicyclopentyl, bicyclohexyl, bicycloheptyl, bicyclooctyl.

Suitable chloromonoolefins which may be condensed with the aforementioned saturated compounds will contain up to 4 carbon atoms and will have the chlorine atom attached to one of the doubly-bonded carbon atoms. Specific examples of these chloromonoolefins will include vinyl chloride, 1-chloro-1-propene, 2-chloro-1-propene, 1-chloro-1-butene, 2-chloro-1-butene and 2-chloro-2-butene.

The catalytic compositions of matter which are used in the process of the present invention comprise organic peroxides which are designated as free radical-generating catalysts. Examples of these catalysts which may be used include, in particular, the disubstituted hydrogen peroxides such as di-t-butyl peroxide, t-butyl perbenzoate, benzoyl peroxide, etc. It is also contemplated within the scope of this invention that hydroperoxides such as acetyl hydroperoxide and t-butyl hydroperoxide may also be used although not necessarily with equivalent results.

The reaction temperatures should be at least as high as the initial decomposition temperature of the free radical-generating catalysts, such as the peroxide compound, in order to liberate and form free radicals which promote the reaction. In selecting the particular reaction temperature for use in the process of the present invention two considerations must be taken into account. First, sufficient energy by means of heat must be supplied to the reaction system so that reactants, namely, the cycloalkyl hydrocarbon and the chloroolefin in which the chlorine is attached to one of the doubly-bonded carbon atoms, will be activated sufficiently for condensation to take place when free radicals are generated by the catalyst. Second, free radical-generating catalysts such as the peroxy compounds, particularly organic peroxides, decompose at a measurable rate with time in a logarithmic function dependent upon temperature. The rate of decomposition can be, and ordinarily is, expressed as the half-life of the peroxide at a particular temperature. For example, the half-life in hours of di-t-butyl peroxide is 17.5 hours at 125° C., 5.3 hours at 135° C., and 1.7 hours at 145° C. (calculated from data for the first 33% decomposition). A reaction system temperature can be selected so that the free radical-generating catalyst decomposes smoothly with the generation of free radicals at a half life which is not too long. In other words, sufficient free radicals must be present to induce the present chain reaction to take place, and these radicals must be formed at a temperature at which the reactants are in a suitably activated state for condensation. When the half life of the free radical-generating catalyst is greater than 10 hours, radicals are not generated at a sufficient rate to cause a reaction of the process of the present invention to go forward at a practical rate. Thus, the reaction temperature may be within the range of from about 50° to about 300° C. and at least as high as the decomposition temperature of the catalyst, by which is meant a temperature such that the half life of the free radical-generating catalyst is not greater than 10 hours. Since the half life for each free radical-generating catalyst is different at different temperatures, the exact temperature to be utilized in a particular reaction will vary. However, persons skilled in the art are well acquainted with the half life versus temperature data for different free radical-generating catalysts. Thus it is within the skill of one familiar with the art to select a particular temperature needed for any particular catalyst. However, the operating temperatures generally do not exceed the decomposition temperature of the catalyst by more than about 150° C. since free radical-generating catalysts decompose rapidly under such conditions. For example, when a free radical-generating catalyst such as t-butyl perbenzoate is used having a decomposition temperature of approximately 115° C. the process is run at a temperature ranging from 115° to about 265° C. When di-t-butyl peroxide having a decomposition temperature of about 130° C. is used, the process is run at a temperature ranging from 130° to about 280° C. Higher reaction temperatures may be employed, but little advantage is gained if the temperature is more than the hereinbefore mentioned 150° C. higher than the decomposition temperature of the catalyst. The resulting chain reaction. In the absence of hydrogen chloride, the following chain reaction occurs:

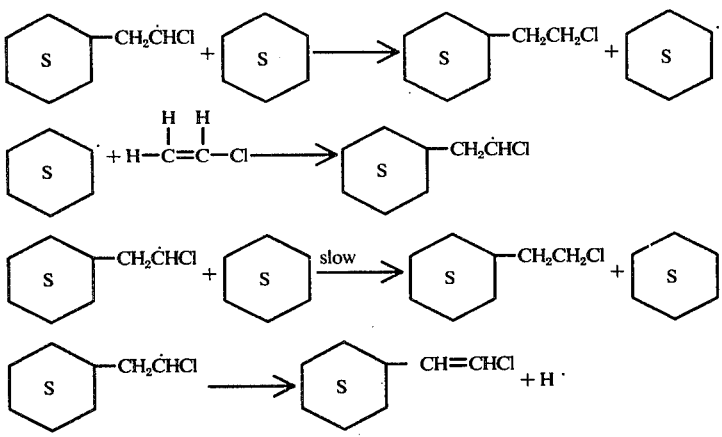

general effect of increasing the operating temperature is to accelerate the rate of condensation reaction between the chloroolefin in which the chlorine atom is attached to one of the doubly-bonded carbon atoms and the saturated compound comprising a cycloalkyl hydrocarbon. However, the increased rate of reaction may be accompanied by a certain amount of undesired side reactions such as polymerization of the chloroolefin.

It is contemplated within the scope of the present invention that a promoter comprising a hydrogen chloride compound will enhance the quantity of monochloro-substituted saturated compound produced in the reaction. By "hydrogen chloride compound" is meant either anhydrous hydrogen chloride or aqueous hydrochloric acid. The effect upon the mechanism of the hereinbefore set forth reaction is that of increasing the yield of the monochloro-substituted product. The mechanism of the action of the hydrogen chloride (which exhibits a marked and unique effect on free radical-induced reactions) is shown by the following example:

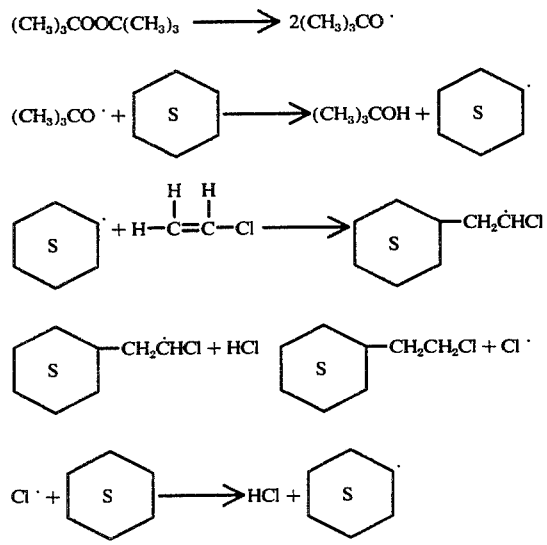

The so-formed cyclohexyl radical starts a new cycle and the (2-chloroethyl)cyclohexane is produced by the The chloroethylcyclohexane radical abstracts a hydrogen atom more rapidly from hydrogen chloride than from cyclohexane and therefore 2-chloroethylcyclohexane is formed more rapidly (and hence in higher yield) than in the absence of hydrogen chloride. The desired compound is then formed before the chloroolefin or the 2-chloroethylcyclohexyl radical undergo polymerization or other side reactions.

The process of this invention may be effected in any suitable manner and may comprise either a batch or continuous operation. For example, when a batch type operation is employed, the reactants comprising the cycloalkyl hydrocarbon and the monochloromonoolefin containing up to 4 carbon atoms in which the chlorine atom is attached to one of the doubly-bonded carbon atoms are placed in an appropriate apparatus along with a free radical-generating catalyst and a promoter comprising a hyrogen chloride compound. In the event that atmospheric pressure is to be employed, the reaction vessel is then heated to a predetermined operating temperature which is at least as high as the decomposition temperature of the free radical-generating catalyst. After maintaining the reactants in the reaction vessel at this temperature for a period of time which may range from about 0.5 up to about 30 hours or more in duration, the heating is discontinued and the vessel is allowed to return to room temperature. The reaction mixture is then recovered, separated from the catalyst and the promoter and subjected to conventional means of purification and separation, said means including washing, drying, extraction, evaporation, fractional distillation, etc., whereby the desired monochloro-substituted saturated compound is recovered. Alternatively, if superatmospheric pressures are to be employed in the reaction, the reactants are charged to a pressure vessel such as a rotating autoclave which contains the free radical-generating catalyst and the hydrogen chloride compound which acts as a promoter. The autoclave is sealed and a substantially inert gas such as nitrogen or helium may be pressed in; the inert gas is added in order to have sufficient pressure at the reactor temperature to maintain a substantial portion of the reactants in the liquid phase. The autoclave is then heated to the desired operating temperature and maintained thereat for a predetermined residence time. At the end of this time, heating is discontinued, the autoclave is allowed to return to room temperature and the excess pressure is discharged. The autoclave is opened and the reaction mixture is then treated in a manner similar to that hereinbefore set forth whereby the desired monochloro-substituted saturated compound is separated and recovered.

It is also contemplated within the scope of this invention that the reaction process for obtaining a monochloro-substituted saturated compound may be effected in a continuous manner of operation. When such a type of process is employed, the reactants comprising a cycloalkyl hydrocarbon and the monochloromonoolefin containing up to 4 carbon atoms in which the chlorine atom is attached to one of the doubly-bonded carbon atoms are continuously charged to a reaction vessel under conditions of continuous agitation as are the free radical-generating catalyst and the promoter comprising a hydrogen chloride compound. If so desired, one or more of the above may be admixed prior to entry into said reaction vessel and the mixture charged thereto in a single stream. After completion of the desired residence time, the reactor effluent is continuously withdrawn and subjected to conventional means of separation whereby the desired monochloro-substituted saturated compound or compounds are recovered, while any unreacted starting material comprising the cycloalkyl hydrocarbon or the monochloromonoolefin are recycled to the reaction zone to form a portion of the feed stock.

Examples of monochloro-substituted saturated compounds which may be prepared according to the process of this invention will include (2-chloroethyl)cyclohexane, x-(1-chloroethyl)-y-(2-chloroethyl)cyclohexane, 1-chloro-2-cyclohexylpropane, 1-chloro-2-cyclohexylbutane, (2-chloroethyl)cycloheptane, (2-chloroethyl)cyclooctane, (2-chloroethyl)decahydronaphthalene, 1-chloro-2-decahydronaphthylpropane, 1-chloro-2-decahydronaphthylbutane, (2-chloroethyl)bicyclohexyl, (2-chloroethyl)bicycloheptyl, 1-chloro-2-cyclopentylbutane, etc. It is to be understood that the aforementioned monochloro-substituted saturated compounds are only representative of the classes of compounds which may be prepared and that the present invention is not necessarily limited thereto.

The following examples are given to illustrate the process of the present invention. However, these examples are not intended to limit the generally broad scope of the present invention in strict accordance therewith.

EXAMPLE I

In this example 100.0 grams (1.19 moles) of cyclohexane, 15 grams (0.24 moles) of vinyl chloride and 6.0 grams of di-t-butyl peroxide were sealed into a glass-lined 850 ml rotating autoclave. The rotating autoclave was heated to a temperature of 130° to 140° C. at an initial pressure of 30 atmospheres of nitrogen for a period of time comprising 4 hours. At the end of this time, heating was terminated and the autoclave vented, thereby allowing said autoclave to return to ambient pressure. The product was recovered and unreacted cyclohexane was distilled off.

The higher boiling residue was analyzed by means of gas-liquid chromatography (which showed the presence of 3 major products of reaction) followed by analysis by mass spectroscopy. About 50% of the 3 major products was (2-chloroethyl)cyclohexane, and about 8% was bis-(2-chloroethyl)cyclohexane and about 12% was tris-(2-chloroethyl)cyclohexane. Minor amounts of more highly chloroethylated cyclohexane compounds were also observed. The presence of higher boiling product was suggested by the fact that when pentane was added to the product remaining after distilling off the cyclohexane, there was precipitated some gummy material; however, the largest portion of the product was the above-discussed (2-chloroethyl)cyclohexanes.

EXAMPLE II

In this example 100.0 grams of cyclohexane, 17.0 grams of vinyl chloride, 6.0 grams of di-t-butyl peroxide and 21.0 grams of concentrated 37% hydrochloric acid in 21.0 grams of water were added to an 850 ml rotating autoclave. The rotating autoclave was heated to a temperature of between 130° and 140° C. at an initial pressure of 30 atmospheres of nitrogen for a period of time comprising 4 hours. At the end of this time, heating was terminated thereby allowing the autoclave to return to room temperature, and the autoclave was vented. The product was recovered and distilled. The material boiling higher than the unreacted cyclohexane was analyzed by means of preparatory gas-liquid chromatography and infrared spectroscopy. The major product showed infrared absorption at 2860 $cm^{-1}$ and 2930 $cm^{-1}$, thereby indicating the presence of a cyclohexyl ring and at 660 $cm^{-1}$ and 730 $cm^{-1}$, thereby indicating the presence of a primary alkyl chloride. It should be noted that the infrared analysis failed to disclose an absorption at 1375 $cm^{-1}$, thereby indicating an absence of methyl grouping. It was determined as a direct conclusion from the infrared analysis that the product (2-chloroethyl)cyclohexane was produced in 30 mole percent yield. The product obtained in lower yield showed infrared absorption at 2860 $cm^{-1}$ and 2940 $cm^{-1}$, thereby indicating the presence of a cyclohexyl grouping, at 450 $cm^{-1}$, thereby indicating the presence of a $CH_2$ bonding and at 615 $cm^{-1}$ and 670 $cm^{-1}$, thereby indicating the presence of a secondary alkyl chloride. It was determined by mass spectroscopy that the largest significant ion found had a molecular weight of 172–174 atomic mass units. It may be concluded from the above infrared and mass spectroscopy data that the product was x-(1-chloroethyl)-y-(2-chloroethyl)cyclohexane which eliminated hydrogen chloride (loss of chlorine attached to the secondary carbon atom) during the mass spectroscopy analysis to form x-vinyl-y-(2-chloroethyl)cyclohexane, the molecular weight of which is 172.8 atomic mass units, in 17 mole percentage yield. It seems probable that bis-(2-chloroethyl)cyclohexane loses hydrogen chloride more readily than does (2-chloroethyl)cyclohexane. In the presence of hydrogen chloride the resulting vinyl compound adds hydrogen chloride to form a (2-chloroethyl)-(1-chloroethyl)cyclohexane. In the absence of hydrogen chloride, the vinyl compound polymerizes.

Contrary to the observation in Experiment I wherein no hydrochloric acid was used, the product of Experiment II remaining after distillation of the unreacted cyclohexane did not yield a gummy precipitate when pentane was added.

EXAMPLE III

The reaction of 21.0 grams of 1-chloro-1-propene with 84.0 grams of cyclohexane in the presence of 6.0 grams of di-t-butyl peroxide using the apparatus and procedure of Example II yielded a mixture of products (named in order of decreasing yield): (A) 1-chloro-2-cyclohexylpropane (13 mole percentage yield), (B)

1-cyclohexyl-1-propene, (C) 2-chloro-1-cyclohexylpropane, (D) a cyclohexylchlorohexane isomer and (E) cyclohexyl chloride.

The reaction was repeated but in the presence of 21.0 grams concentrated hydrochloric acid and 17.0 grams of water. The same products were obtained but in different proportions and yield. A larger amount of the chlorine-containing products was obtained. Named in order of decreasing yields, the products were A (10 mole percent yield), C, D, B, and E.

Similarly, the reaction of 2-chloro-1-propene (which may have contained some 1-chloro-1-propene) yielded (1) in the absence of hydrochloric acid: C (8 mole percent yield), A (7 mole percent yield), D, B, and E; and (2) in the presence of 21.0 grams concentrated hydrochloric acid and 20.0 grams water: A (7 mole percent yield), C (6 mole percent yield), D, B, and E.

EXAMPLE IV

In this example 138 grams (1.0 mole) of decahydronaphthalene, 15 grams (0.24 mole) of vinyl chloride, 6.0 grams of peroxide and 21 grams of concentrated 37% hydrochloric acid in 21 grams of water may be sealed into the glass liner of a rotating autoclave. The autoclave may be pressured by the addition of 30 atmospheres of nitrogen following which it is heated to a temperature of about 80° C. and maintained thereat for a period of 4 hours. At the end of the 4-hour period, the heating may be terminated and the autoclave is allowed to return to room temperature. Following return to room temperature, the autoclave may be vented to remove excess pressure and the reaction mixture may be recovered therefrom.

The reaction mixture which is recovered from the autoclave may then be subjected to distillation to remove unreacted decahydronaphthalene and the residue subjected to analysis by means of preparatory gas-liquid chromatography and infrared spectroscopy. The product will show the presence of (2-chloroethyl)-decahydronaphthalene.

EXAMPLE V

In a manner similar to that set forth in the above examples, 97 grams (0.5 mole) of bicycloheptyl, 7.5 grams (0.12 mole) of vinyl chloride, 6 grams of di-t-butyl peroxide and 21 grams of concentrated hydrochloric acid in 21 grams of water may be placed in an autoclave which is thereafter sealed and heated to a temperature between 130° and 140° C. under an imposed pressure of 30 atmospheres of nitrogen. The autoclave may be maintained at this temperature for a period of 4 hours, following which heating is discontinued and the autoclave is allowed to return to room temperature. The excess pressure may then be vented and the autoclave opened. The reaction mixture which is recovered may then be subjected to distillation to remove unreacted bicycloheptyl, water and hydrochloric acid. Analyses of the residue by means of preparatory gas-liquid chromatography and infrared spectroscopy may then disclose the presence of (2-chloroethyl)bicycloheptyl.

EXAMPLE VI

In this example 70 grams (1.0 mole) of cyclopentane, 22.5 grams (0.25 mole) of 1-chloro-1-butene, 6 grams of benzoyl peroxide and 20 grams of concentrated 37% hydrochloric acid in 21 grams of water may be treated in a manner similar to that set forth in the above examples, that is, by placing the reactants in the glass liner of a rotating autoclave, sealing said autoclave, pressuring with 30 atmospheres of nitrogen and heating to a temperature between 80° and 90° C. After maintaining the autoclave at this temperature range for a period of 4 hours, heating may then be discontinued and the autoclave allowed to return to room temperature. After venting the excess pressure from the autoclave, it is opened and the reaction mixture may then be recovered therefrom. After distillation to remove unreacted cyclopentane, the residue may then be subjected to analytical methods similar to those set forth above. Said methods may then disclose the presence of the desired product comprising 1-chloro-2-cyclopentylbutane.

We claim as our invention:

1. In a process for the production of a monochloro-substituted saturated compound which is effected by condensing a saturated cycloalkyl hydrocarbon selected from the group consisting of a cycloalkane having from 5 to about 8 carbon atoms in the ring, a bicycloalkyl having from 10 to 16 carbon atoms in the rings and a polycycloalkane having from 6 to 14 carbon atoms in the rings with a chloromonoolefin possessing not more than 4 carbon atoms and having the chlorine atom attached to one of the doubly-bonded carbon atoms in the presence of a free radical-generating peroxide catalyst at a temperature at least as high as the decomposition temperature of said catalyst and a pressure of from 1 to about 100 atmospheres, and recovering the resultant monochloro-substituted saturated compound, the improvement which comprises effecting the reaction in the presence of a promoter comprising hydrogen chloride.

2. The process as set forth in claim 1 in which said peroxide catalyst is di-t-butyl peroxide.

3. The process as set forth in claim 1 in which said peroxide catalyst is benzoyl peroxide.

4. The process as set forth in claim 1 in which said cycloalkyl hydrocarbon is cyclohexane and said chloromonoolefin is vinyl chloride.

5. The process as set forth in claim 1 in which said cycloalkyl hydrocarbon is cyclohexane and said chloromonoolefin is 1-chloro-1-propene.

6. The process as set forth in claim 1 in which said cycloalkyl hydrocarbon is decahydronaphthalene and said chloromonoolefin is vinyl chloride.

7. The process as set forth in claim 1 in which said cycloalkyl hyrocarbon is bicycloheptyl and said chloromonoolefin is vinyl chloride.

8. The process as set forth in claim 1 in which said cycloalkyl hydrocarbon is cyclopentane and said chloromonoolefin is 1-chloro-1-butene.

* * * * *